United States Patent
Blank et al.

(10) Patent No.: US 8,067,937 B2
(45) Date of Patent: Nov. 29, 2011

(54) PROBE AND SYSTEM FOR ELECTRON SPIN RESONANCE IMAGING

(75) Inventors: Aharon Blank, Kfar-Vradim (IL); Lazar Shtirberg, Nesher (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 12/304,770

(22) PCT Filed: Jun. 14, 2007

(86) PCT No.: PCT/IL2007/000726
§ 371 (c)(1),
(2), (4) Date: Jul. 6, 2009

(87) PCT Pub. No.: WO2007/144890
PCT Pub. Date: Dec. 21, 2007

(65) Prior Publication Data
US 2010/0001728 A1  Jan. 7, 2010

Related U.S. Application Data

(60) Provisional application No. 60/813,696, filed on Jun. 15, 2006.

(51) Int. Cl.
*G01V 3/00* (2006.01)
(52) U.S. Cl. .......................... 324/316; 324/321
(58) Field of Classification Search .................. 324/316, 324/321
See application file for complete search history.

(56) References Cited

U.S. PATENT DOCUMENTS

| 4,280,096 | A | * | 7/1981 | Karthe et al. ................. 324/316 |
| 5,610,522 | A |   | 3/1997 | Locatelli et al. |
| 5,889,402 | A | * | 3/1999 | Kumatoriya et al. ......... 324/321 |
| 6,704,594 | B1 |  | 3/2004 | Blank et al. |
| 7,403,008 | B2 | * | 7/2008 | Blank et al. .................. 324/316 |
| 2005/0021019 | A1 |  | 1/2005 | Hashimshony et al. |

FOREIGN PATENT DOCUMENTS

| EP | 0399789 | 11/1990 |
| WO | WO 2005/117698 | 12/2005 |

OTHER PUBLICATIONS

International Preliminary Report on Patentability Dated Dec. 31, 2008 From the International Bureau of WIPO Re.: Application No. PCT/IL2007/000726.
Blank et al. "A Three-Dimensional Electron Spin Resonance Microscope", Review of Scientific Instruments, 75(9): 3050-3061, 2004. p. 3055-3056.
Blank et al. "Pulsed Three-Dimensional Electron Spin Resonance Microscopy", Applied Physics Letters, 85(22): 5430-5432, 2004.

(Continued)

*Primary Examiner* — Louis Arana (57) ABSTRACT

ESR imaging probe, system, and method are described. The probe is an ex-situ probe, the system comprises the probe and configured for operating the probe, and the method comprises detecting ESR from outside a resonator of the probe. An exemplary embodiment of a probe according to the invention comprises a cooled dielectric resonator, and one sided gradient coils. An exemplary embodiment of the system comprises source current that is configured to supply to the gradient coils currents of up to 100 A in pulses shorter than 1 μsec.

29 Claims, 8 Drawing Sheets

OTHER PUBLICATIONS

Blank et al. "Transparent Miniature Dielectric Resonator for Electron Paramagnetic Resonance Experiments", Review of Scientific Instruments, 74(5): 2853-2859, 2003.

Casanova et al. "Two-dimensional Imaging With a Single-Sided NMR Probe", Journal of Magnetic Resonance, Academic Press, 163(1): 38-45, 2003. Chap.3.1, 3.3, Fig.2.

Sakran et al. "Electron Spin Resonance Microscopic Surface Imaging Using a Microwave Scanning Probe", Applied Physics Letters, 82(9): 1479-1481, 2003.

Communication Pursuant to Article 94(3) EPC Dated Mar. 10, 2011 From the European Patent Office Re. Application No. 07736465.1.

Egorov et al. "Measuring the Dieletric Permittivity of Sapphire at Temperatures 93-343 K", Radiophysics and Quantum Electronics, 44(11): 885-891, 2001.

Response Dated Sep. 12, 2011 to Communication Pursuant to Article 94(3) EPC of Mar. 10, 2011 From the European Patent Office Re. Application No. 07736465.1.

\* cited by examiner

PROBE AND SYSTEM FOR ELECTRON SPIN RESONANCE IMAGING

RELATED APPLICATIONS

This Application is a National Phase of PCT Patent Application No. PCT/IL2007/000726 having International filing date of Jun. 14, 2007, which claims the benefit of U.S. Provisional Patent Application No. 60/813,696 filed on Jun. 15, 2006. The contents of the above Applications are all incorporated herein by reference.

FIELD OF THE INVENTION

The present invention relates to ESR imaging and in particular to a probe and a system for ESR imaging and a method of producing an ESR image.

BACKGROUND OF THE INVENTION

Electron spin resonance imaging (ESR imaging) is a technique for obtaining spatially resolved ESR-based data from samples. ESR-based data is data obtained by applying on the sample a static magnetic field, exciting electron spins in the sample by electromagnetic waves, and detecting irradiation created by the electron spins as a result of their excitation.

The spatially resolved ESR-based data can, for example, provide information about chemical structure, eluci date biological functions, enable non-invasive medical diagnosis, and be used to solve material science problems.

In classical ESR detection method, termed "induction detection", the imaged specimen is put inside a microwave resonator, and is subjected to a static magnetic field and to microwave radiation. Within the framework of "induction detection", there are two possible schemes to obtain the ESR-based data, pulsed and continuous wave ESR. In pulsed ESR, a specific set of microwave pulses are induced upon the sample and after a short while the spins in the sample create microwave radiation of their own, termed "echo", which is concentrated by the resonator and analyzed. In continuous wave (CW) ESR, the sample is irradiated with a continuous microwave irradiation, and the ESR signal is detected by monitoring the microwave signal reflected from the resonator.

To obtain spatial information on the location of the spins that create the ESR signal, one can make use of the fact that the frequency of the ESR signal changes with the intensity of the magnetic field. Specifically, a combination of static and time varying magnetic field gradients are applied across the specimen, such that each point (voxel) in the specimen is exposed to a magnetic field with different intensity at different times. This way, spins from each voxel irradiate in a different frequency or with different phase, and the frequency or phase is used to determine the location of the spins that created the signal.

The magnetic field gradients are usually applied with gradient coils. The stronger is the gradient provided by the gradient coils, the better is the spatial resolution of the obtained ESR image.

An imaging device, designed to image a specimen when the specimen is inside the imaging device, is said to have in-situ geometry. An imaging device, designed to image a specimen when the specimen is outside the imaging device is said to have an ex-situ geometry. In the context of induction ESR, a specimen is said to be inside the imaging device if it is inside the smallest is convex volume that includes the resonator, the gradient coils, and the static magnetic field source.

Applicant is not aware of any ESR imaging device, which operates in the induction detection method and has ex-situ geometry.

One drawback of the in-situ geometry is the need to insert the specimen into the imaging device. This limits the size of the specimen, or requires a large device.

A drawback of induction detection is its notoriously low Signal-to-Noise-Ratio (SNR), which requires, under ambient conditions, to sense at least $10^7$ spins per voxel. These SNR limitations are also reflected by the limited image resolutions currently achievable with induction detection-based electron spin resonance imaging.

The best available resolution for induction detection was achieved in a system described in US patent application publication No. 2006-0022675 (hereinafter US '675), wherein the present inventor is a co-inventor. This publication describes room temperature in-situ ESR imaging probe, for biological applications, having a resolution of the order of $(1\ \mu m)^3$.

In recent years, new ESR detection methods were introduced, which, under extreme physical conditions, or for unique samples, can greatly improve the sensitivity and the image resolution of magnetic resonance. These methods include, for example, Scanning Tunneling Microscopy-ESR (STM-ESR), Magnetic Resonance Force Microscopy (MRFM), Hall detection, Optically Detected Magnetic Resonance, quantum dot spin detection, and electrically detected magnetic resonance.

This wide variety of techniques, however, has very limited spectroscopic and 3D imaging capability, and often requires very complicated sample preparation procedures, which makes its practical use very difficult.

WO2005/073695 describes an on-chip magnetic resonance spectroscopy in ex-situ geometry, but does not provide imaging possibilities, and does not operate in the induction detection method.

WO02/21147 describes an ex-situ microwave microscope capable of detecting ESR signals using induction detection, but at very low resolution and without ex-situ static magnetic field source and gradients.

SUMMARY OF THE INVENTION

An aspect of some embodiments of the invention relates to ESR imaging that utilizes an induction detection method and provides exceptionally high sensitivity and resolution. In exemplary embodiments of the invention, the ESR imaging probe is sensitive to as few as 100-1000 spins per voxel for 60 min acquisition at cryogenic temperature. In an exemplary embodiment of the invention, the ESR imaging probe provides within one hour acquisition at cryogenic temperatures images having a resolution of at least $[1000\ nm]^3$, preferably at least $[100\ nm]^3$, and under some circumstances even $[10\ nm]^3$. For example, if the spins has relaxation times in the order of 1-5 μsec, an exemplary probe is sensitive to about 1000 spins, which at spin concentration of $6 \times 10^{17}$ spins/cc, provides resolution of 100 nm×100 nm×100 nm. Longer relaxation times and higher spin concentration are associated with higher resolution. Compromising the resolution along one of the axes may allow better resolution along the other axes. For instance, in the example provided above, resolution of 400 nm×50 nm×50 nm may be obtained.

In an exemplary embodiment of the invention, the ESR probe utilizes a cooled dielectric resonator.

Cooling the resonator optionally comprises contacting the resonator with a cryogenic fluid, such as nitrogen vapor, helium vapor, or the like.

Cooling the resonator according to embodiments of the present invention increases the resonator's permittivity and quality factor, and this improves the sensitivity of the resonator and allows working with smaller resonators than those useful with lower permittivity materials or at higher temperatures.

Smaller resonators allow closer positioning of gradient coils. When the distance between the coils and the specimen is short, the coils provide at the specimen larger gradients, and allow better spatial resolution. Thus, providing cooled dielectric resonators according to some embodiments of the present invention allows exceptional sensitivity and resolution.

An aspect of some embodiments of the invention relates to ex-situ ESR imaging. In an ex-situ ESR imaging probe according to exemplary embodiments of the invention, the resonator concentrates microwave signals arriving from a specimen positioned outside the resonator well enough to allow producing an image of the specimen based on the ESR signals. In this context, "well enough" mainly means with high enough SNR, for instance, 2 or more, preferably, 5 or more, more preferably 10 or more.

In an exemplary embodiment of the invention, the probe is configured for imaging a sample that lies outside the probe, namely, the probe has an ex-situ geometry.

Optionally, both the gradient coils and the static magnetic field source are positioned on one side of the sample. Alternatively, the gradient coils are positioned on one side of the sample, preferably near the resonator, and the static magnetic field source is on the other side of the sample.

In a preferred embodiment of the invention, the probe is self-contained, in the sense that the magnet, the microwave feed, the gradient coils, and the resonator, are all compactly arranged to move as a single unit. Optionally, the single unit is small, and can be packed in a package of about 5×5×5 cm.

In an exemplary embodiment of the invention, the resonator is made of high-permittivity materials and small dielectric losses. Preferably, the resonator is cooled as to improve SNR of signals arriving from outside the resonator. Optionally, cooling is to cryogenic temperatures.

Optionally, the gradient coils are single-sided coils, extending only on one side of the resonator. Examples to known coils that may be used as one-sided coils are dissected Maxwell pair and Golay coils. The single-sided coils are preferably ex-situ coils, which provide gradient fields outside the probe, at the sample.

According to some embodiments of the invention, an ex-situ ESR imaging probe comprises a microwave feed, and a microwave shield, shielding the resonator from microwave radiation other than that coming from the microwave feed and preventing radiation from the feed to the outside of the imaging probe and away of the sample. In some embodiments, this shield is only on one side of the resonator, and the probe is configured to image a specimen put on the other side. In other embodiments, a microwave shield exists also at the specimen's side of the resonator, but without shielding the specimen from the resonator, for instance, behind the specimen.

Exemplary embodiments of the invention may be used to examine semiconductor devices with a high spatial resolution. Semiconductor devices may be examined, for example, for 3-D distribution of paramagnetic impurities (introduced to the semiconductor intentionally by doping or unintentionally), defects, and other sites with un-paired electrons, and for metal contacts or layers. Optionally, such examination is carried out during the development process of new circuits or circuit components. Alternatively or additionally, such examinations may take place in the production line, for instance, in conjunction with existing online semiconductor inspection machines Exemplary embodiments of the invention may find utility in the field of materials science research, such as surface science and polymer science, as a laboratory analytical tool, and/or in production facilities, as a quality assurance—QA tool.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of exemplary embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF EXEMPLARY EMBODIMENTS

In the following description subtitles are provided to ease the reading of the detailed description, however, these subtitles are not intended to limit the interpretation of the terms used herein, or to provide basis for interpreting any term.

Figure 1A:
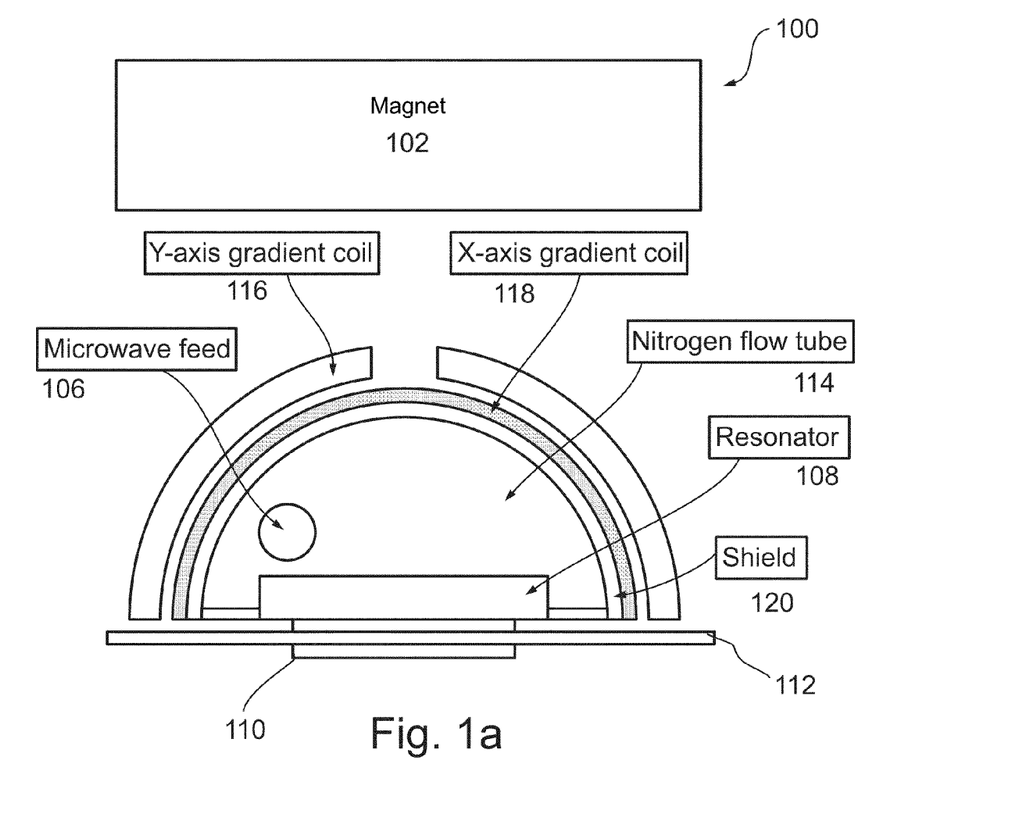
FIG. 1A is a schematic illustration of a cross-section in an ESR imaging probe according to an exemplary embodiment of the invention.
Figure 1B:
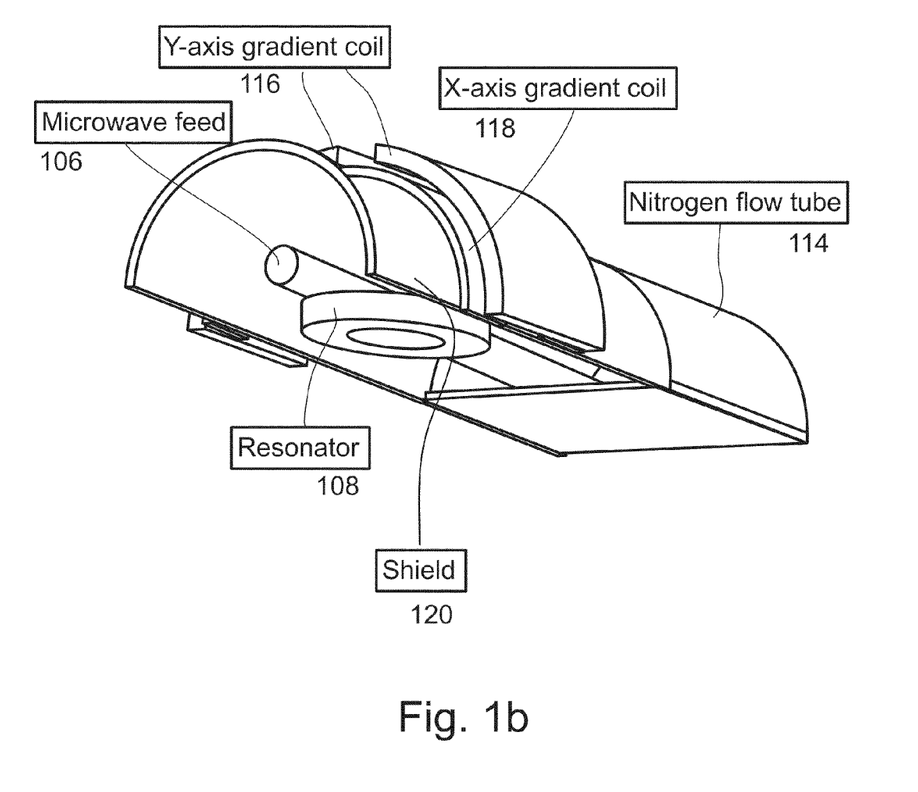
FIG. 1B is an isometric view of an ESR imaging probe, according to an embodiment of the invention.

FIG. 1A is a schematic illustration of a cross-section in an ESR imaging probe 100 according to an exemplary embodiment of the invention. FIG. 1B is an isometric view of a similar probe, not comprising the permanent magnet. In this embodiment, the static magnetic field is provided by a source that does not form part of the probe.

Figure 4:
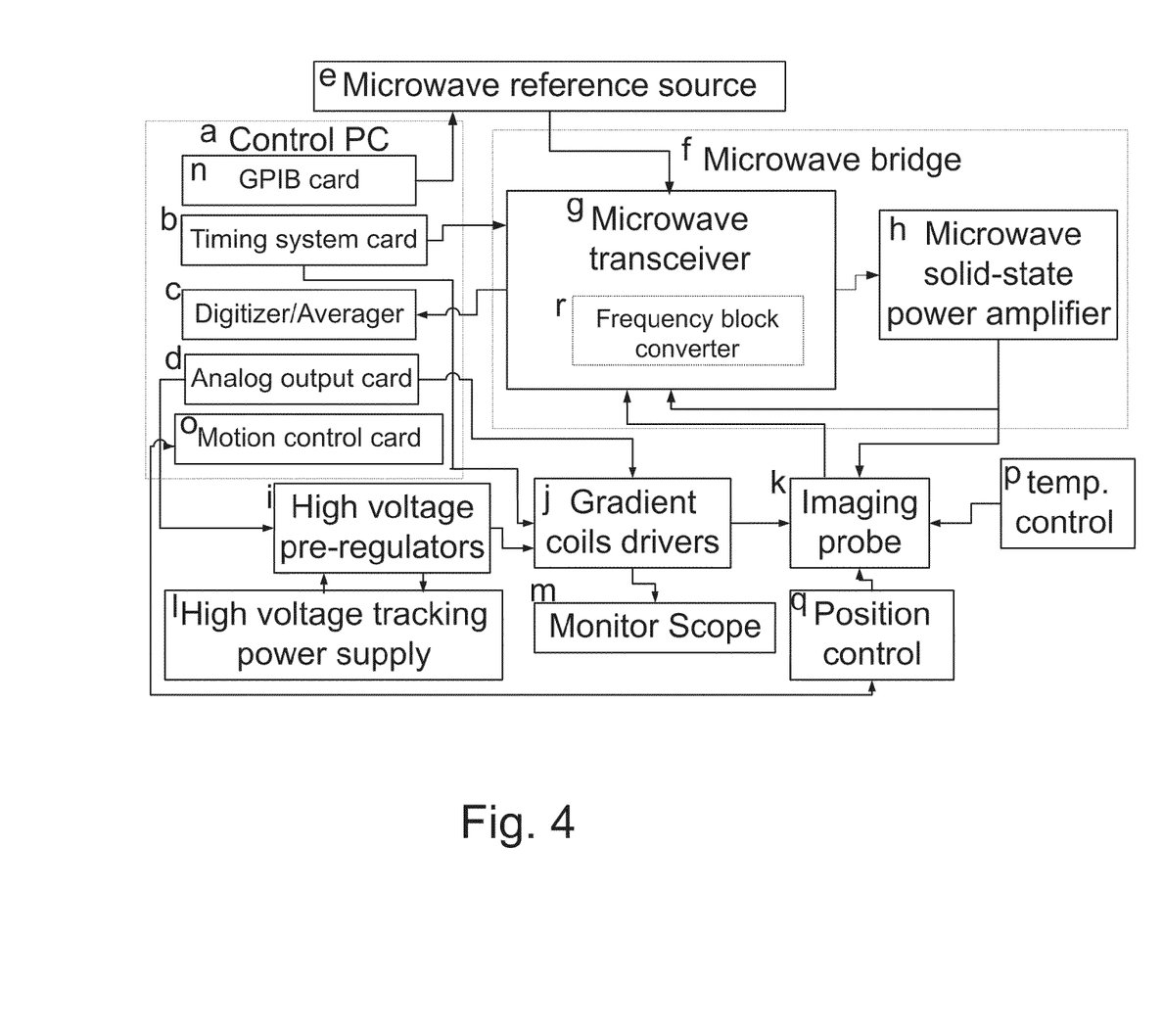
FIG. 4 is a block diagram of an imaging system according to an embodiment of the invention.

Probe 100 comprises a permanent magnet 102, a microwave feed 106, a resonator 108, and a connection (see line going from k to g and from there g to c in FIG. 4) to a processing unit (c in FIG. 4).

In an exemplary embodiment of the invention, probe 100 is provided as an integral unit, with magnet 102 attached to the other probe parts as to move with them. In this embodiment, a scan of specimen may be provided by moving probe 100 from one spot to another on the specimen. For this, probe 100 may be mounted on a scanner arm (308 in FIG. 3). Probe 100 optionally fits into a small package having a volume of about 10 liter, 1 liter, 0.1 liter, or any intermediate size.

The Permanent Magnet

Figure 2A:
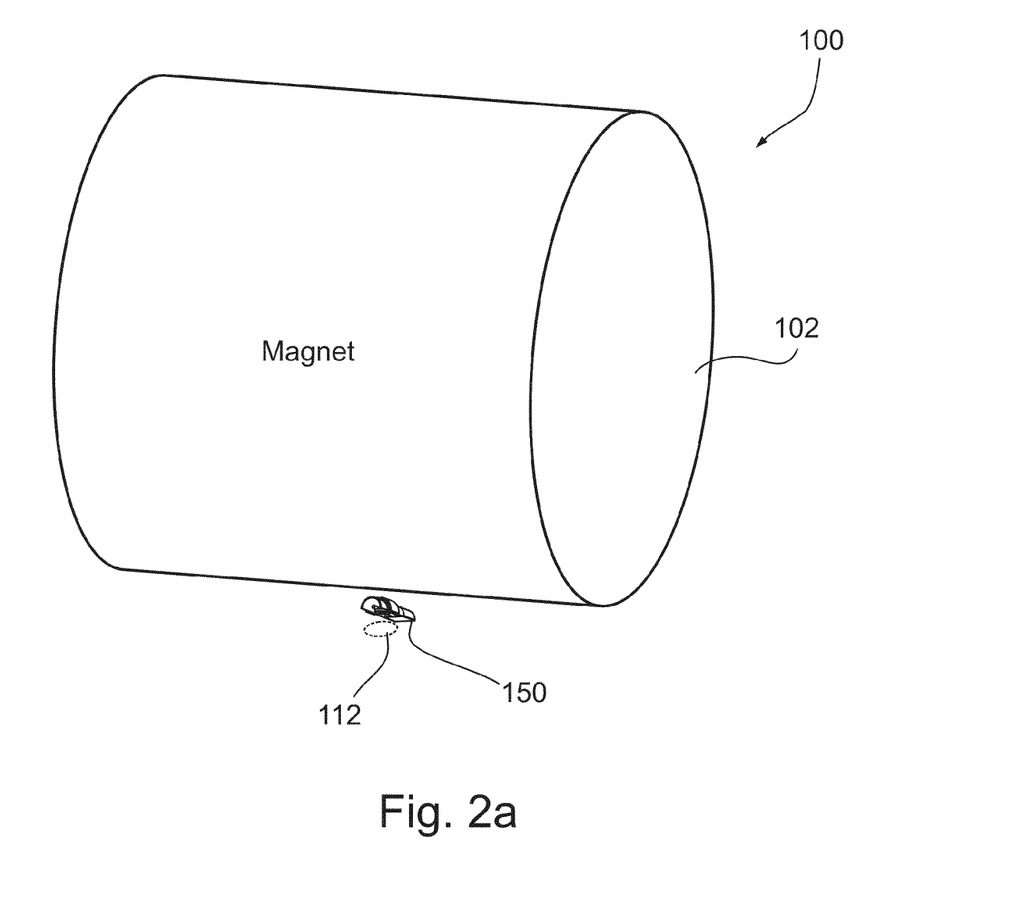
FIG. 2A is an isometric illustration of an ESR imaging probe according to an embodiment of the invention.

Permanent magnet 102, shown to scale with other parts of probe 100 on FIG. 2A, provides a static magnetic field around itself, thus defining a statically magnetized region. In alternative embodiments of the invention, permanent magnet 102 may be replaced with an electromagnet, which at operation provides a static magnetic field by means of current flow through the coils of the electromagnet.

Figure 2B:
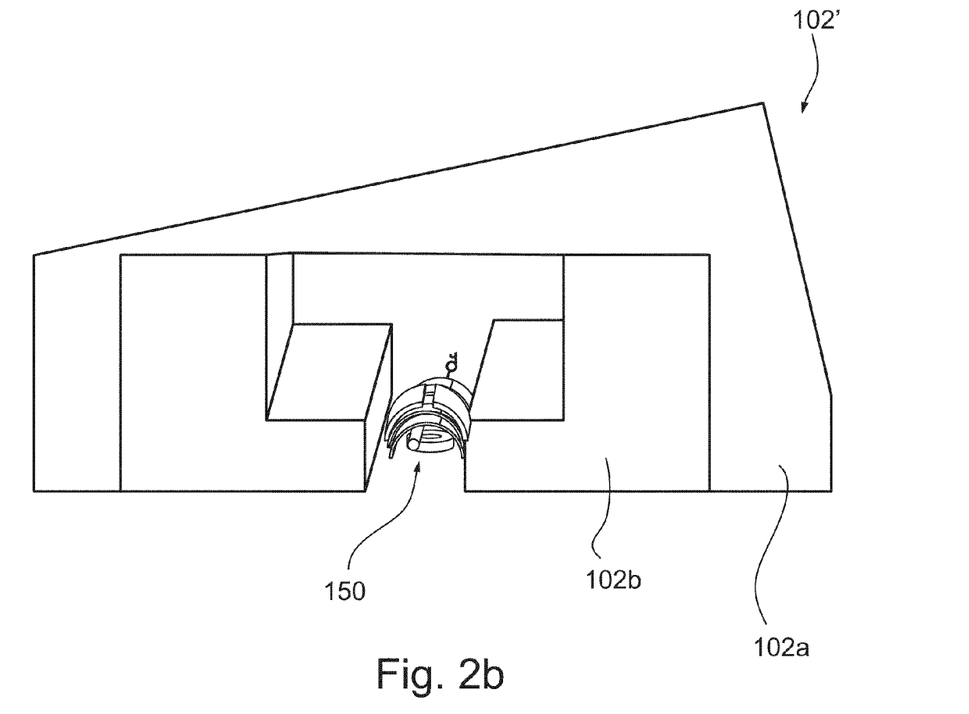
FIG. 2B is a schematic illustration of an ESR imaging probe according to another embodiment of the invention.

FIG. 2A is an isometric illustration of probe 100, where the permanent magnet is drawn to scale with the other parts of the probe. Permanent magnet 102 is shown as a cylinder of 30 mm in diameter and 60 mm in height. FIG. 2B is a schematic illustration of an ESR imaging probe having an integral permanent magnet 102' having a different configuration. Magnet 102' has soft iron/steel part 102A and rare earth magnets 102B. The other parts of the probe are shown small and collectively marked as 150. Similar reference numerals are used in FIGS. 1A, 1B, 2A and 2B to denote similar parts.

The Microwave Feed

The microwave feed, 106, adequately conveys microwave energy from a microwave bridge to the resonator. Optionally, the microwave feed comprises transmission line, for example, waveguide, or coaxial cable. Optionally, the microwave feed is an output of a microwave bridge, the bridge itself being part of the probe. For example, in case the transmission line is a coaxial line the microwave feed is optionally a small closed loop formed by connecting the central conductor of the coaxial cable to the outer one. Alternatively, the microwave feed is a straight feed going from the central conductor of a coaxial cable. In case of a waveguide transmission line, the microwave feed is optionally an extended dielectric rod antenna coming out of the waveguide. In exemplary embodiments of the invention, the microwave feed is configured to feed microwave around the resonance frequency of the resonator, which is typically between about 10 GHz and about 60 GHz. The microwave feed is connected to a transceiver, which transmits microwave for exciting the spins, and receives the signal from the spins.

The Resonator

Resonator 108 is optionally a ring resonator, with a diameter of between about 0.1 mm and about 3 mm, for instance 1 mm. The height of the resonator is optionally from about 0.1 mm to about 1.5 mm, for instance, 0.35 mm.

In an exemplary embodiment of the invention, the resonator is a single ring resonator, machined from a single crystal of a substance having high permittivity and small dielectric losses, for example, $SrTiO_3$ (Commercial Crystals, Fla. USA), permittivity of about 300 at room temperature and tan δ (a quantity used in the field of electromagnetics to describe the dielectric losses) of about $5 \times 10^{-4}$.

The preferred dimensions of the resonator depend upon the material from which it is made and the required resonance frequency. For example if one employs $TiO_2$ as material for the resonator, and the required resonance frequency is 17.5 GHz, than the diameter of the ring is ~2.6 mm and its height is ~0.5 mm (for operation at room temperature). A resonator made of the same material and configured for imaging at 35 GHz and cryogenic temperatures is optionally 0.35 mm in height and about 1.1 to 1.2 mm in diameter.

Resonator 108 is preferably machined from single crystals, which at cryogenic temperature under about −150° C. have permittivity ($\in$) of about 200 to about 10,000 and quality factor (Q) of about 1,000 to about 100,000. For both permittivity and quality factor, higher values are preferred. Some examples of relevant materials having these properties can be $SrTiO_3$, $KTaO_3$, $TiO_2$, and Ba—Nd—Ti—O.

Resonator 108 is configured to concentrate magnetic alternating fields created by microwave feed 106 when exciting the spins and concentrate the ESR signal created by the spins back to the feed when the spins irradiate. The effect of field concentration is strong enough such that the intensity of the alternating magnetic field outside the volume of the resonator, for instance, at a region of interest marked in the drawing as 110, is good enough to obtain ESR signals in a specimen 112 placed in an imaging proximity to the resonator. Imaging proximity, in this context, is a distance of between about 1 and about 10, 100, or 200 μm, with shorter distances allowing higher resolution. The ESR signals are strong enough and have high enough SNR to be used for creating an image of the specimen portion where statically magnetized region, region of interest 110, and specimen 112, overlap. The terms "outside the volume of the resonator", "near the resonator", and the like, refer to places that are outside the smallest convex body that includes the resonator.

Optionally, the ESR signals are of a frequency of about 9 to 60 GHz, optionally between 16 and 60 GHz.

Cooling

FIGS. 1A and 1B also show a tube 114, configured to carry to resonator 118 cold fluid, for example nitrogen gas at 77K or helium gas at 4K, or any other inert cryogenic fluid, depending on the temperature to which the resonator is to be cooled. Optionally, tube 114 is in fluid communication with a cryogenic fluid source (not shown). The cryogenic fluids may be used in their liquid and/or gas phase.

Gradient Coils and Drivers

Probe 100 optionally comprises gradient coils 116 and 118. As may be seen in FIG. 1B, gradient coils 116 and 118 are single-sided coils, that extend only above resonator 108. Coil 116 provides a magnetic field with a gradient along the Y axis, coil 118 provides a magnetic field with a gradient along the X axis. Permanent magnet 102 functions as a gradient source to provide a gradient along the Z axis. This gradient is constant in time.

The resonator and gradient coils can work in both CW and pulse mode. The x-axis gradient coil (118) is a simple "Maxwell pair" sliced into half, so instead of a full circle, each winding goes along only half a circle. The y-axis gradient coil (116) is one half of a standard "Golay" type gradient coil.

Preferably, the inductance of the coils in CW mode is about 10-100 μH, while in pulse mode coils with inductance of about 1-10 μH are preferred.

Coils 116 and 118 are operable to produce gradients of about 10-20 T/m-A, so that a current of up to 100 A peak can be used to generate a gradient of about 1000-2000 T/m. In accordance with ESR imaging theory, such gradients are sufficient to provide spatial resolution of up to 10 nm, depending on the specific characterization of the imaged specimen. In pulse ESR imaging mode these gradients are optionally 100-1000 ns in duration. Small duty cycle of the gradient operation (typically <1%) ensures that ohmic coil heating does not harm the coils. In CW ESR imaging mode, ensuring low level of ohmic is heating comprises switching the gradients on and off in the ms time scale.

Figure 5:
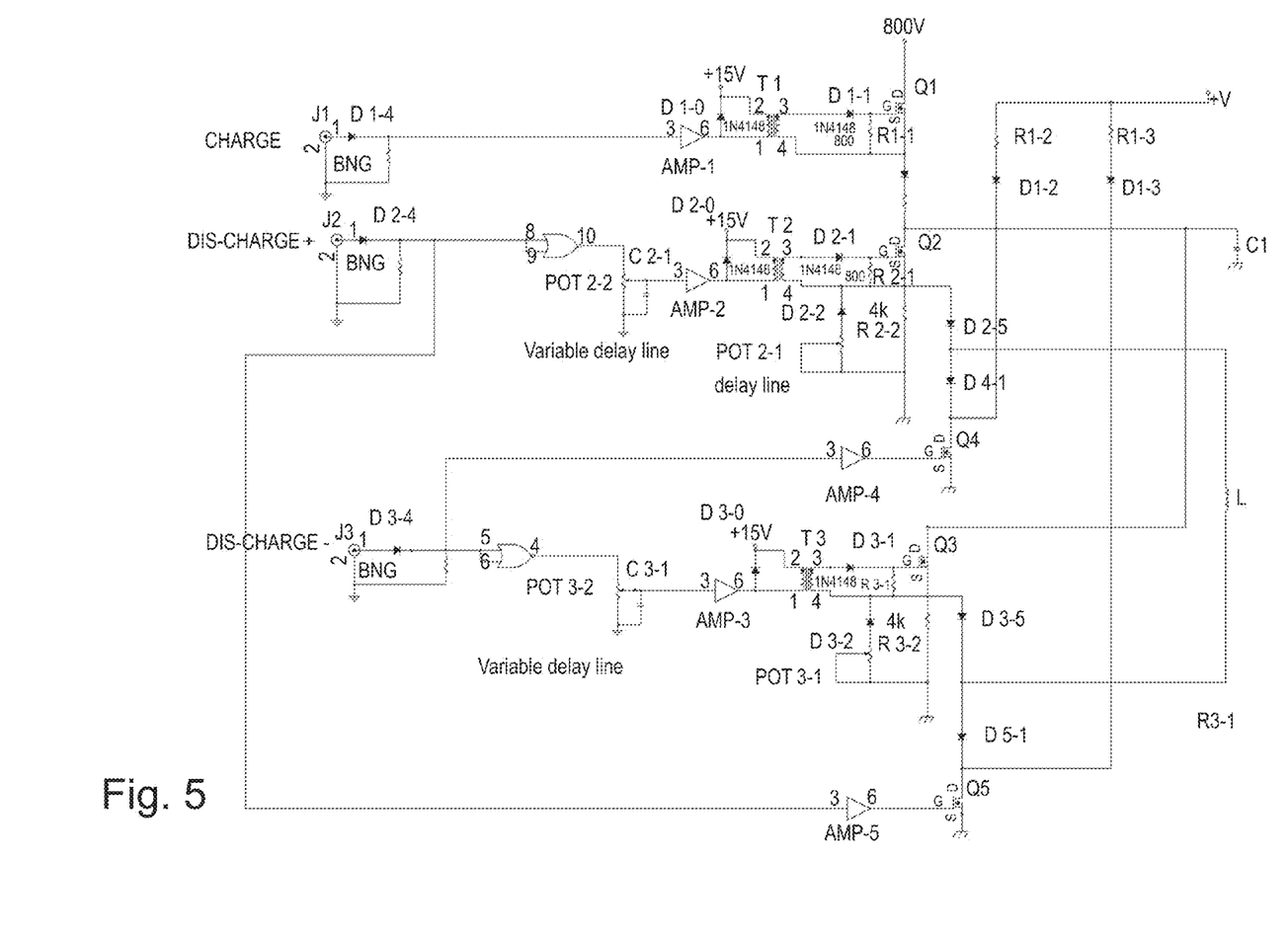
FIG. 5 is an electronic scheme of a gradient coil driver for use in an exemplary embodiment of the invention.

To produce fast and strong magnetic field gradients in pulsed mode, system 500 is optionally equipped with gradient current drivers 514 of the kind described in FIG. 5.

FIG. 5 is an electronic scheme of a gradient coil driver for use in an exemplary embodiment of the invention. A driver as described in FIG. 5 is configured to produce very short pulses, of about 100-2000 ns with a peak of up to 100 A, and with duty cycle of up to 50 kHz. In operation, a driver as shown in FIG. 5 operate as follows:

Initially only Q1 is turned on, and current is going from the high voltage source (800V) to charge capacitor C1. When C1 is fully charged, a discharge command is applied. The discharge can be either with positive or negative polarity. In case of a positive polarity, the switches Q2 and Q5 are turned ON. The capacitor C1 discharges through Q2, D2-5, L, D5-1, and Q5 to the ground. The current through L generates the required strong and short gradient pulse. Similar discharge command, which turns ON Q3 and Q4 is applied to obtain a negative current flow through L. By changing the voltage charge of C1 and/or the polarity of the current flow, one can obtain a full range of positive or negative magnetic field gradient values.

The Shield

Probe 100 optionally comprises a microwave shield 120 for shielding resonator 120 from magnetic fields coming from outside of probe 100. Shield 120 reduces the radiation losses of the resonator and also helps lowering the noise in the signals obtained by resonator 108, and this way improves the SNR. Shield 120 is preferably transparent to the magnetic fields generated by the gradient coils. In an exemplary embodiment, shield 120 is a 0.2 μm thick gold foil. Optionally, an imaging system with a probe similar to that of FIG. 1 comprises a metal ground plane (not shown) for placing the specimen thereon and providing microwave shielding on the other side of the specimen.

Exemplary Imaging Systems

Figure 3:
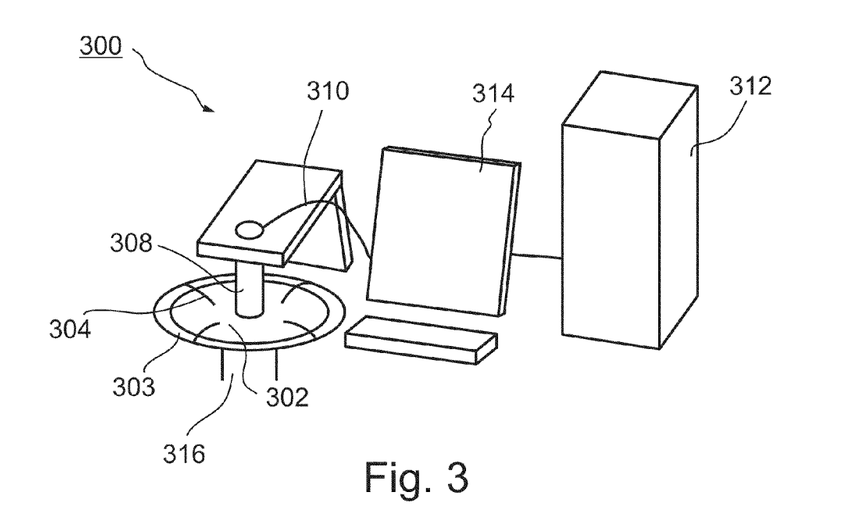
FIG. 3 is a schematic illustration of an imaging system according to an embodiment of the invention.

FIG. 3 is a schematic illustration of an imaging system 300 according to an embodiment of the invention, with a sample 302 fixed to a tray 303 with mechanical fixtures 304. System 300 comprises a probe (not shown, as it is attached to the sample) mounted on a positioning arm (308). Optionally, positioning arm 308 is mounted on driving means, configured to drive arm 308 both in parallel to sample 302 and perpendicular to it, such that the arm can bring the probe just above the sample, and also move in parallel to the sample's surface from one point to another.

Sample 302 optionally comprises one or more of a semiconductor wafer, a printed circuit board, a crystal, and polymer doped with paramagnetic substances.

Sample 302 is attached to tray 303 with mechanical fixtures 304, which optionally comprises hooks 304 or vacuum suction means (not shown).

Tray 303 optionally comprises a metal layer which functions as a shield, preventing microwave energy transmitted by spins in sample 302 to go down and away of the probe.

Tray 303 is optionally mounted on a vertical member 316, which optionally is moveable up and down to assist in bringing the probe and the sample in close proximity.

Probe 306 is according to an embodiment of the invention, and connected with a transmission line 310 to the Control PC and microwave system, shown together as 312. The image is optionally displayed on the PC display 314.

FIG. 4 is a block diagram of an imaging system according to an embodiment of the invention, operating in pulsed mode.

In overview, the operation of the pulsed ESR imaging system of FIG. 4 may be described as follows:

The system computer (a) through the motion control card (o) positions the probe (k) at the proper location by the position control system (q). In addition, the temperature is set to the appropriate operating temperature by the temperature controller (p). Optionally, temperature controller p is also controlled by computer a.

In order to obtain high resolution ESR image at the location of the probe, the system computer (a) controls the timing system card (b) to initiate an imaging pulse sequence in the microwave bridge transceiver (g) and in the pulse gradient current driver unit (j). The excitation pulses (after amplification in amplifier h) and the gradient currents go into the imaging probe (k).

The echo signal from the imaging probe (k) is detected in the transceiver (g), sampled and averaged by the fast digitizer (c) and then processed in the computer (a).

In operation, the timing system controls the operation of the microwave bridge, which transmits the microwave pulses in a user specified phase and receives the ESR echo signal. The power output of the power amplifier (h) is sufficient to provide hard 90° pulses of about 10-100 ns with the small resonator used. The pulsed gradient coils in the imaging probe (k) are driven by one or two pairs (j) of gradient coil drivers for driving one or both of the x axis and the y axis coils. The gradient coil drivers are fed by pre-regulated high voltage power supplies. A gradient coil driver (j) has four channels. Two of the channels can generate large (up to ~100 A peak) half sine current pulses by pre-charging a capacitor and subsequently discharging it into the gradient coil (optionally by the circuit described in FIG. 5). For each channel the capacitor voltage is determined by the pre-regulated high voltage power supply (i), and is proportional to the analog voltage it receives from the analog-output card (d). The two remaining channels are optional, and can be used to lock the resonator to the frequency of the ESR signal, by producing relatively small (up to 3 A) constant DC current into one of the axes of the gradient coils and optionally into a bias coil.

Figure 6:
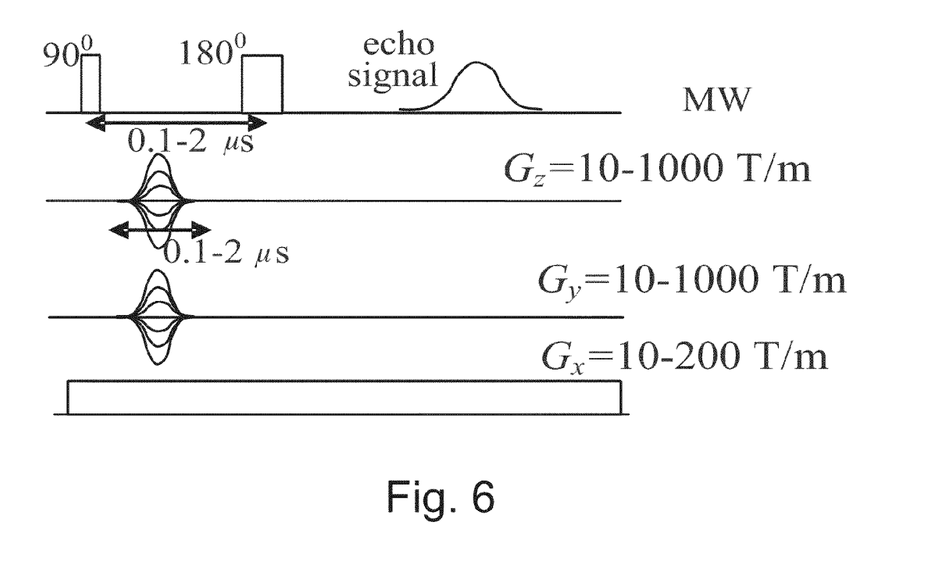
FIG. 6 is a graphic representation of an exemplary pulse sequence used for pulsed ESR imaging in accordance with an embodiment of the invention.

FIG. 6 is a graphic representation of an exemplary pulse sequence and gradients that may be used for producing an image with the system of FIG. 4 and circuit of FIG. 5.

In operation, the probe is brought to a distance of about 10-100 microns above the surface of the examined sample, and measures (at a single location) a cylindrical volume, referred to as instantaneous field of view (FOV). Optionally, the dimensions of the cylinder are about 0.1 mm in diameter and about 10 microns in height (inside the sample).

The detected signals are optionally analyzed using ESR imaging theory, to provide the location and type of paramagnetic centers (e.g. crystal defects, impurities or doping atoms, and/or conduction electron of metals) with a resolution of ~10-100 nm and a sensitivity of 1-1000 paramagnetic centers (spins) per voxel (as detailed above). The obtained image is then optionally displayed on a physical, such as a computer monitor or a print out. Additionally or alternatively, the obtained picture is saved, as to allow displaying the image at a later stage, further processing it with image processing tools, etc.

In order to achieve these performances the probe is preferably cooled to about 77K or lower temp, optionally by means of Nitrogen or Helium flow system, and the acquisition time is in the order of tens of minutes. Shorter acquisition times can be employed at the expense of sensitivity and image resolution.

Figure 7:
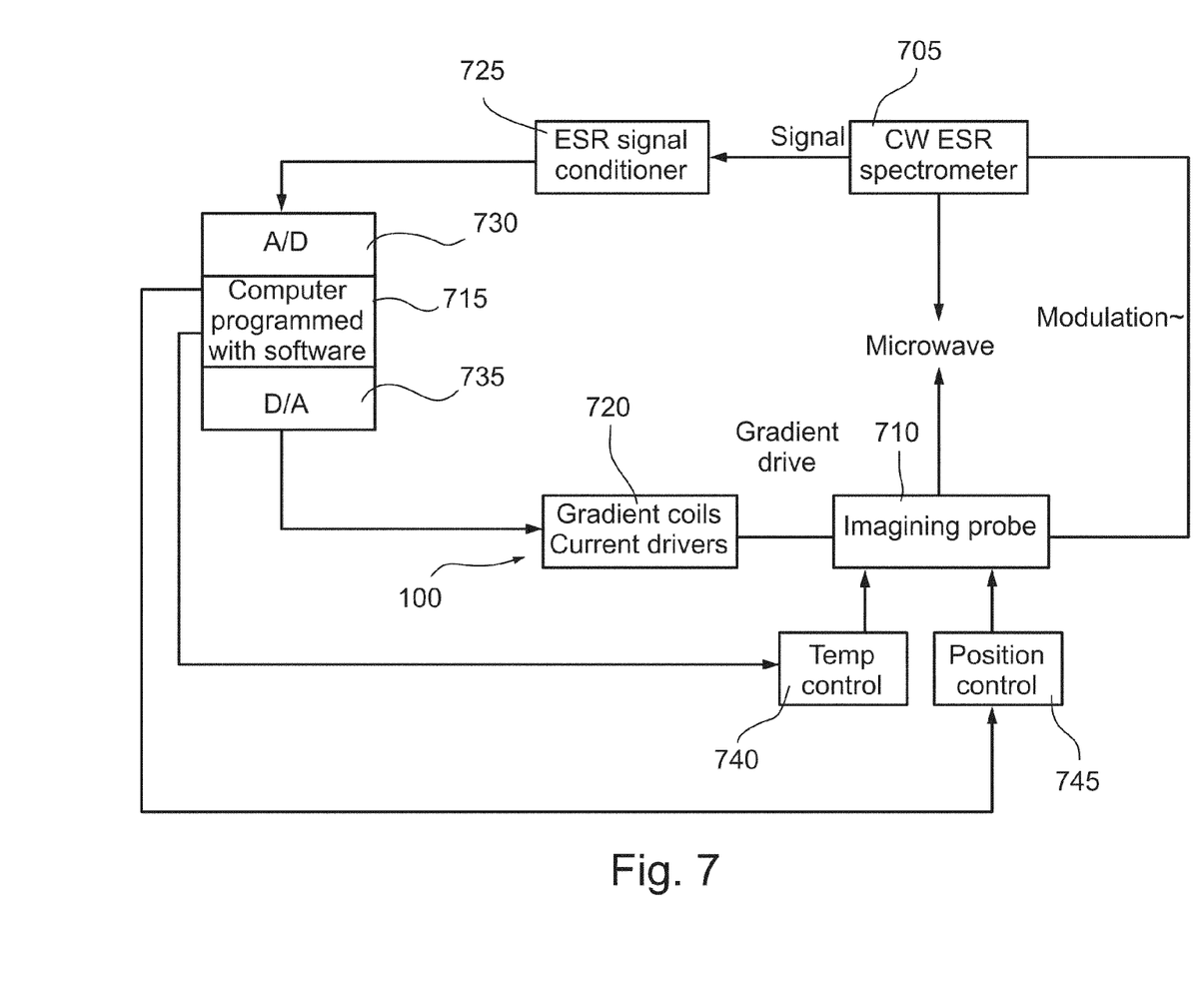
FIG. 7 is a block diagram of a CW-ESR imaging system according to an embodiment of the invention.

FIG. 7 is a block diagram of an imaging system 700 according to an embodiment of the invention, operating in CW mode.

The CW ESR Imaging system comprises: (a) a conventional CW ESR spectrometer 705, for example a commercially available CW ESR spectrometer such as a Varian, Bruker, or JEOL instrument, modified with: (b) an imaging probe 710, preferably in accordance with one of the embodiments of the invention; (c) a dedicated computer 715 which controls the imaging process and acquires the ESR signal; (d)

at least one current driver 720 for the gradient coils (and preferably one current driver for each gradient coil); (e) a baseband (up to 250 kHz) amplifier and filter unit (signal conditioner 725) which obtains the raw ESR signal from the CW ESR spectrometer and preconditions it to enable the signal to be digitized, for example by an A/D card; (f) a position control 740 for controlling the relative position between imaging probe 710 and the sample; and (g) a temperature control 745 for controlling the temperature of the probe to be below about −150° C.

The computer can be any commercially available general purpose programmable computer having sufficient computational power to perform the required computations. The computer can be, for example, a desktop computer, a laptop computer, or another commercially available computation device having memory for holding programmed instructions and data, and input and output ports and devices for accepting instructions from a user and for reporting information to the user in any convenient form. The computer can run data acquisition software (for example LabView version 7 software available from National Instruments, or another user interface comprising a graphical user interface (GUI)), and comprises an analog-to-digital (A/D) card 730 (for example, the PCI-6023 from National Instruments) for data digitization and acquisition. The computer also comprises a digital-to-analog (D/A) card 735 (for example, a PCI analog output card with 8 outputs and an update rate of up to 200 kHz, such as the PCI-6713 from National Instruments) to generate analog output signals, such as the gradient waveforms for the imaging axes and the waveform for the modulation coil. The current waveform in the gradient coils can be generated either directly at the computer analog output card or in a control unit as described in the alternative embodiment hereinbelow.

In operation, probe 710 is placed near a sample and the sample and the probe are positioned one in relation to the other with position control 745. Temperature control 740 controls the temperature at the probe to be cryogenic temperature. The CW ESR spectrometer 700 applies electromagnetic energy to the imaging probe 710 and receives return signals. The return signals are communicated to the ESR signal conditioner 725 and then passed to the A/D 730 for digitization. The digital signals produced are communicated to the computer 715, which is operating software to analyze the digital signals and to display results to a user. The computer 715 can also communicate control signals to the imaging probe 710 by way of D/A 735 that converts digital signals generated by the computer 715 to analog signals that are communicated to the current drivers 720 which control the signals applied to gradient coils operating in conjunction with the imaging probe. The gradient coils apply gradient signals to the imaging probe 710, thereby spatially encoding the signal detected by the CW ESR spectrometer 705. The spatially encoded signals are then fed back to the computer 715. A user or a programmed sequence can command the computer 715 to modify the gradients according to principles that will allow the detection of useful spatially-encoded ESR information about the sample of interest.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The terms "specimen" and "sample" are used herein interchangeably.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An ESR imaging probe comprising: a microwave feed, a resonator and a connector, wherein said microwave feed is configured to transmit microwave energy to said resonator in order to obtain ESR signals by exciting electron spins in a region of interest;

wherein said resonator is configured for concentrating said ESR signals generated at said region of interest, and for acquiring a signal from 1000 electron spins or less within one hour;

wherein said connector is configured to send to a processor an input indicative of said ESR signals, so as to allow the processor to generate an image of a sample portion overlapping said region of interest from said ESR signals; and wherein said probe is configured for imaging a sample portion outside the smallest convex volume that includes the resonator.

2. An ESR imaging probe according to claim 1, comprising a source of static magnetic field.

3. An ESR imaging probe according to claim 2, wherein said source of static magnetic field comprises an electromagnet.

4. An ESR imaging probe according to claim 2, being a self-contained ex-situ probe wherein said microwave feed, said resonator and said source of static magnetic field are all arranged to move as a single unit.

5. An ESR imaging probe according to claim 2, further comprising at least one gradient coil, and being a self-contained ex-situ probe wherein said microwave feed, said resonator, said source of static magnetic field and said at least one gradient coil are all arranged to move as a single unit.

6. An ESR imaging probe according to claim 2, wherein said static magnetic field provides a static magnetic field around itself, thus defining a statically magnetized region, and wherein said statically magnetized region and said region of interest overlap.

7. An ESR imaging probe according to claim 2, wherein said source of static magnetic field comprises a permanent magnet.

8. An ESR imaging probe according to claim 1, wherein said image has a resolution of at least 100 nm×100 nm×100 nm.

9. An ESR imaging probe according to claim 1, wherein said resonator is a ring dielectric resonator.

10. An ESR imaging probe according to claim 1, wherein said resonator comprises at least one high permittivity substance, which at temperatures below −150° C. have permittivity of 200-10,000 and quality factor of 1,000-10,000.

11. An ESR imaging probe according to claim 1, wherein said resonator has a diameter of 3 mm or less.

12. An ESR imaging probe according to claim 1, comprising at least one gradient coil to spatially encode the ESR signals from the sample.

13. An ESR imaging probe according to claim 12, being a self-contained ex-situ probe wherein said microwave feed, said resonator and said at least one gradient coil are all arranged to move as a single unit.

14. An ESR imaging probe according to claim 12, wherein said gradient coil is a single-sided ex situ coil.

15. An ESR imaging probe according to claim 12, wherein at least one of said at least one gradient coil is one half of a Maxwell pair.

16. An ESR imaging probe according to claim 12, wherein at least one of said at least one gradient coil is configured for creating magnetic gradients of between 10 and 1000 T/m in pulses of between 0.1 and 2 μsec.

17. An ESR imaging probe according to claim 1, comprising a microwave shield shielding one side of the resonator from microwave irradiation.

18. An ESR imaging probe according to claim 17, wherein said microwave shield is transparent to radiation originated by the magnetic field gradient source.

19. An ESR imaging probe according to claim 1, comprising a cooler for cooling said resonator to a temperature below −150° C.

20. An ESR imaging system comprising an ESR imaging probe according to claim 1.

21. An ESR imaging system according to claim 20, comprising a mechanical fixture to fix a surface of the sample to the outside of the resonator.

22. An ESR imaging system according to claim 20, comprising a microwave shield on both sides of the resonator.

23. An ESR imaging system according to claim 20, comprising a position controller configured to control a relative position between a sample and the probe.

24. An ESR imaging system according to claim 20, comprising a temperature controller configured to control the temperature of said resonator to a cryogenic temperature.

25. An ESR imaging system according to claim 20, and having a gradient coil connected to a current source capable of providing a current pulse having a peak at 30 A or more and a duration of less than 1000 ns.

26. An ESR imaging system according to claim 25, wherein said peak is at 100 A.

27. A method of producing an image of at least a portion of a sample, the method comprising:
  (a) bringing the sample and a resonator of an ESR imaging probe into imaging proximity while keeping said sample out of the resonator, said resonator being configured to acquire from the sample a signal from 1000 electron spins or less within one hour; and
  (b) operating the ESR imaging probe to excite spins in said sample to produce ESR signals; and
  (c) processing said ESR signals to produce an image.

28. A method according to claim 27, wherein operating comprises cooling said resonator to a cryogenic temperature.

29. A method according to claim 27, wherein keeping said sample out of said resonator comprises fixing the sample and the resonator at a distance of at least 1 μm from each other.

* * * * *